United States Patent [19]

Jennings et al.

[11] Patent Number: 4,727,136
[45] Date of Patent: Feb. 23, 1988

[54] MODIFIED MENINGOCOCCAL GROUP B POLYSACCHARIDE FOR CONJUGATE VACCINE

[75] Inventors: Harold J. Jennings, Gloucester; Rene Roy, Gatineau; Andrzej Gamian, Ottawa, all of Canada

[73] Assignee: Canadian Patents and Development Ltd., Ottawa, Canada

[21] Appl. No.: 782,384

[22] Filed: Oct. 1, 1985

[51] Int. Cl.$^4$ .................... C07K 15/04; C07K 39/095; C07K 39/108; C07H 1/00
[52] U.S. Cl. ............................. 530/395; 530/350; 530/403; 530/405; 530/806; 530/825; 424/88; 424/92; 536/1.1; 514/23
[58] Field of Search .......... 424/88, 92; 435/849, 435/871; 530/350, 825, 395, 403, 405, 806; 536/1.1; 514/23

[56] References Cited

U.S. PATENT DOCUMENTS 4,185,090 1/1980 McIntire ............................ 424/88
4,356,170 10/1982 Jennings et al. .................... 424/88
4,545,985 10/1985 Pastan et al. ....................... 424/88

OTHER PUBLICATIONS

Jennings et al, *I. Immunol.*, 134, 1985, pp. 2651–2657.
Lifely et al, *Carbohydrate Res.*, 94, 1981, pp. 193–203.
Isai et al, *J. Bacteriology*, 146, 1981, pp. 69–78.
Frasch, *Semin. Infert. Dis.*, 2, 1979, pp. 304–337.

*Primary Examiner*—John Kight
*Assistant Examiner*—Garnette D. Draper
*Attorney, Agent, or Firm*—Alan A. Thomson

[57] ABSTRACT

The group B polysaccharide of *Neisseria meningitidis* is chemically modified to enhance the immune response thereto, thereby providing cross-reactive antibodies of high affinity. The N-acetyl group of the sialic acid residues of the polysaccharide has been substituted by the N-propionyl group, and this modified antigen then conjugated to a physiologically-acceptable protein such as tetanus toxoid. This conjugate vaccine has been found to raise high titers of high affinity group B IgG antibodies and would be useful against meningitis caused by group B *N. meningitidis* or by *E. coli* KI organisms.

8 Claims, No Drawings

MODIFIED MENINGOCOCCAL GROUP B POLYSACCHARIDE FOR CONJUGATE VACCINE

This invention is directed to a vaccine from chemically modified group B polysaccharides of *Neisseria meningitidis*. The modified polysaccharide is conjugated to a protein carrier to provide the vaccine.

BACKGROUND AND PRIOR ART

Although the groups A, C, Y and W135 capsular polysaccharides of *N. meningitidis* have been used with some success in providing homologous serogroup immunity in humans, the group B polysaccharide is only poorly immunogenic.

The poor immunogenicity of the group B meningococcal polysaccharide (GBMP) and the structurally identical *E. coli* KI capsular polysaccharide (1, 2, 3) preclude their use as vaccines against meningitis caused by group B meningococcal (GBM) and *E. coli* KI organisms. Although GBM organisms are able to produce low levels of GBMP-specific antibodies in animals and humans, these antibodies are, with one notable exception, almost exclusively IgM and of relatively low affinity (4). Recently Frosch et al. (5) reported that GBMP-specific monoclonal antibodies of the IgG isotype could be readily produced by injecting a specialized strain of autoimmune NZB mice with GBM organisms. The poor immunogenicity of these polysaccharides is probably attributable to tolerance due to cross-reactive tissue components because of the identification of structurally similar $\alpha$-(2$\rightarrow$8)-linked oligomers of sialic acid in the gangliosides of human and animal fetal brain tissue (6,7). This structural mimicry probably also accounts for the importance of these capsular polysaccharides as virulence factors in the GBM and *E. coli* KI organisms (3). Because of the poor immunogenicity of the GBMP, other strategies to produce a GBM vaccine have been explored, including the use of serotype protein antigens alone (8) and in combination (9, 10) with the GBMP, and the use of serotype lipooligosaccharides conjugated to protein carriers (11).

Chemical manipulation of the GBMP has been tried in which it was covalently coupled to tetanus toxoid (2). However, this type of conjugation failed to enhance the immunogenicity of the GBMP to the desired degree (2, and vide infra).

Improvement in the immune response by structural modification within the GBM polysaccharide apparently has not been attempted so far and this invention is an initial development in this direction. It would be desirable to further chemically modify the GBM polysaccharide prior to its conjugation in such a way as to make significant structural changes in it, while still being able to retain its antigenicity to group GBM polysaccharide-specific antibodies. Thus the modified polysaccharide-conjugate could conceivably elicit more cross-reactive antibodies to the native GBM polysaccharide than the native GBM polysaccharide-conjugate itself.

SUMMARY OF THE INVENTION

This invention comprises a process for modifying a group B polysaccharide of *Neisseria meningitidis* comprising (a) deacetylating N-acetyl groups in sialic acid residues of the group B polysaccharide, and (b) N-propionylating the deacetylated polysaccharide to give an N-propionyl-group B meningococcal polysaccharide.

The invention provides a modified group B polysaccharide of *Neisseria meningitidis* having sialic acid residue N-acetyl groups replaced with N-propionyl groups.

The process of the invention includes the further step of conjugating the N-propionyl polysaccharide to an immunologically-suitable protein carrier.

Another part of the invention is the antigenic conjugate comprising the modified group B polysaccharide of *Neisseria meningitidis* having sialic acid residue N-acetyl groups replaced with N-propionyl groups conjugated to an immunologically-suitable protein carrier.

A cross-reactive vaccine may be prepared comprising this conjugate suitable e.g. for humans.

Experiments indicate that the N-propionyl-GBMP-protein conjugate induced higher levels of GBMP-specific antibodies in rabbits than the homologous GBMP-protein conjugate. In addition the native GBMP bound more strongly to these cross-reactive antibodies than to antibodies raised to its own homologous protein conjugate. Further tests with the N-propionyl conjugate antigen in mice showed high levels of cross-reactive GBMP-specific IgG antibodies were produced. Two populations of antibodies were observed in mice, one specific for the N-propionyl GBMP and the other cross-reactive with N-acetyl GBMP. It was found possible to boost the level of these antibodies with successive immunizations.

DETAILED DESCRIPTION

The group B meningococcal polysaccharide can be isolated from *N. meningitidis* cultures for example as outlined in J. Biol. Chem. 249; 4797–4801 D. R. Bundle et al According to the invention, this native polysaccharide first is N-deacetylated to provide a reactive amine group in the sialic acid residue parts of the molecule. This deacetylation may be carried out for instance in a basic aqueous medium at elevated temperatures preferably about 90°–110° C. with the pH 13–14.

The base suitably is an alkali metal hydroxide, particularly sodium hydroxide of about 2M concentration. The degree of deacetylation may vary from about 30% to about 100% depending on the conditions. It is preferred to achieve about 90–100% deacetylation. The N-deacetylated product may be recovered e.g. by cooling, neutralization, purification if desired, and lyophilization.

Next this N-deacetylated GBMP is N-propionylated by reaction with propionic anhydride (or propionic adic) usually in an aqueous medium at substantially neutral pH e.g. pH of about 6.5–8. The reaction medium can be purified if desired e.g. by dialysis, and the N-propionylated product recovered e.g. by lyophilization. The degree of N-propionylation achieved can vary from about 90–100%. Propionyl chloride also is a suitable reactant.

The following reaction scheme summarizes these two reactions. Yields approaching 100% have been obtained from both reactions.

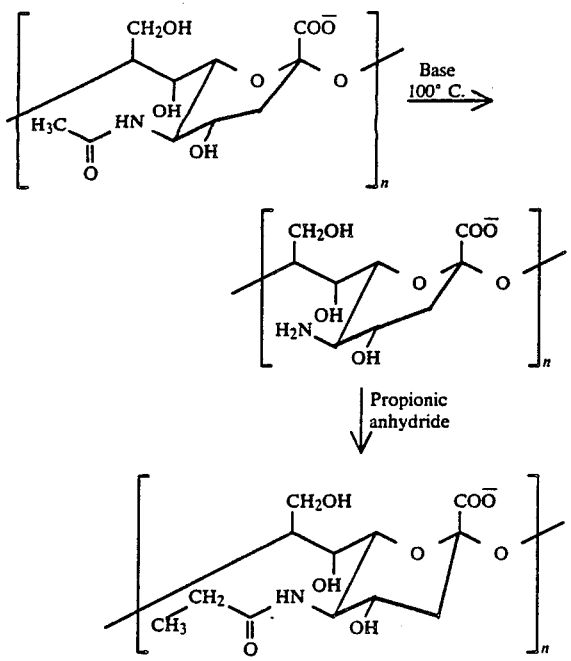

The molecular weight of the N-propionyl polysaccharide usually is within the range of about 10,000 to about 50,000.

It has been found necessary, as a third step, in order to prepare a beneficial antigen or vaccine, to conjugate the N-propionyl —GBMP with a suitable protein carrier. The carrier may be any physiologically-tolerated protein which can be coupled to the polysaccharide. Preferably, the protein is itself an immunogen. Suitable proteins include tetanus toxoid (TT), diphtheria toxoid and other proteins derived from bacteria.

In U.S. Pat. No. 4,356,170 October 26, 1982 Jennings et al, the conjugation of polysaccharides modified to have terminal aldehyde groups, with the amino groups of proteins, by reductive amination, has been described. This is a preferred mode of conjugation according to this invention. The polysaccharide and protein become covalently linked through a

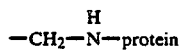

linkage. However other modes of conjugation are possible.

The N-propionyl-polysaccharide-protein conjugate has been tested in in vitro assays, in rabbits, and in mice and has been found to have improved immunogenic properties, compared to the N-acetyl (native) and N-deacetylated polysaccharides and to their polysaccharide-protein conjugates. The test procedures and results are given in the Examples.

For vaccine use the conjugate may be administered by injection in any suitable carrier such as physiological saline or other injectable liquids e.g. subcutaneously, intraperitoneally or intramuscularly. Additives customarily used in vaccines may be present e.g. stabilizers and adjuvents. The conjugate may be part of a of a composite vaccine e.g. for humans.

For vaccine purposes, a suitable dosage usually would fall within the range of from about 5 to 25 micrograms for humans.

The following examples are illustrative.

EXAMPLE 1

*N. meningitidis* strain 608 (b) was grown in a chemically defined medium, and the cetavlon(TM)-precipitated capsular polysaccharide GBMP was purified by extraction with hot buffered phenol and treatment with ribonuclease as described in Bundle et al loc. cit.

N-Deacetylation of the GBMP

The GBMP (Na+salt) (200 mg) was treated with 10 mL of 2M NaOH at 105°-110° C. as described in J. Immunol. 134: 2651 (1985) H. J. Jennings et al. Samples were withdrawn at time intervals, neutralized with hydrochloric acid, dialyzed for 3 d at 4° C. against ammonium bicarbonate (pH 7.5), and lyophilized. The degree of N-deacetylation in each sample was determined from their $^1$H-nmr spectra using the intensity ratio of the methyl acetamido signals of the sialic acid residues (singlet at $\delta$ 2.07) with the $H_{3e,3a}$ proton signals of the same residues at $\delta$ 2.66 and $\delta$ 1.72 respectively. Fully N-deacetylated GBMP was obtained after 6 h of hydrolysis as determined by the absence of the methyl acetamido signal in the $^1$H-nmr spectrum of this signal.

N-Propionylation of the GBMP

N-Deacetylated GBMP (50 mg) was dissolved in 10 mL of saturated aqueous sodium bicarbonate solution and two aliquots (0.25 mL) of propionic anhydride were added to the solution at 15 min intervals with constant stirring. Stirring was continued overnight, after which time the reaction gave a negative ninhydrin test. The solution was dialyzed against distilled water and lyophilized to yield N-Pr GBMP (54 mg). A series of partial N-propionylations were also carried out and the degree of N-propionylation in them was determined from their $^1$H-nmr spectra by comparing the intensities of the $CH_3$- and $CH_2$-propionamido signals at $\delta$ 1.12 and $\delta$ 2.32 respectively, with those of the $H_{3e,3a}$ signals of the sialic acid residues at $\delta$ 2.65 and $\delta$1.73 respectively. In the fully N-propionylated GBMP this ratio was 5:2.

EXAMPLE 2

Polysaccharide conjugates

A terminal aldehyde group was introduced into the N-Ac GBMP and N-Pr GBMP by controlled periodate oxidation (see U.S. Pat. No. 4,356,170). Through this group the polysaccharides were conjugated to TT (tetanus toxoid) by reductive amination as described in this patent except that the time required for conjugation (5 d) was found to be considerably shorter. The M-Ac GBMP-TT and N-Pr GBMP-TT conjugates had molar ratios of polysaccharide to TT of 1:2.3 and 1:5 respectively, as determined from the sialic acid to protein ratio.

EXAMPLE 3

RABBIT IMMUNIZATION TESTS

Immunological properties of the conjugates

The native and N-Pr-GBM polysaccharide-TT conjugates were used as immunogens in rabbits and the antisera were evaluated by quantitative precipitin and radio-labelled binding assays.

Immunization procedures

Three Californian rabbits were immunized subcutaneously with the conjugate of Example 2 in Freund's complete adjuvant (Difco, Detroit, MI) and bled according to previously described procedures (5).

Immunological methods

Quantitative microprecipitin experiments were carried out according to the method of Kabat and Mayer (i.e. Kabat, E. A., and M. M. Mayer. 1961. Experimental Immunochemistry, 2nd ed., p. 2, Charles C. Thomas, Publisher, Springfield, Ill.) using 0.1 mL of antiserum. The antigen-binding assay was carried out using a modification (12) (13) by mixing in Eppendorf microtest tubes (Brinkmann Instruments Inc., Westburg, NJ) 50 µL of a solution containing 250 ng of the [$^3H$]-labelled GBM polysaccharide and serial dilutions of rabbit conjugate and control antiserum made up to a total volume of 550 µL. Following incubation at 4° C. for 16 h, an equal volume of saturated (at 4° C.) ammonium sulfate was added to the tubes and they were agitated and left to stand at 4° C. for 30 min. The tubes were centrifuged at 15,000 rpm for 10 min. and two aliquots of 400 µL were withdrawn from each tube, The aliquots were mixed with 4 mL of a scintillant-containing xylene and the mixtures were counted in a liquid scintillation counter.

The precipitin curves of a typical rabbit N-Pr-GBM-TT conjugate antiserum with both the native and N-Pr-GBM polysaccharide were obtained. While the N-Pr-GBM polysaccharide precipitated in excess of 500 µg of antibody/mL from its homologous antiserum, the native GBM polysaccharide was also able to precipitate significant quantities (100 µg/mL) of antibody from the same antiserum. No precipitation was observed in any of the preimmune sera.

These precipitin analyses indicated that the N-Pr polysaccharide conjugate not only elicited very high levels of antibody to its homologous polysaccharide but also raised significantly higher levels of native GBM polysaccharide-specific antibodies than was previously found for the native GBM polysaccharide-TT conjugate itself.

Cross-reactions of the native GBM polysaccharide and its N-Pr analog were also exhibited in the following antigen binding assays. In these studies the ability of [$^3H$]-labelled native GBM polysaccharide to bind to both the rabbit N-Pr and native group GBM-TT conjugate antisera were studied and the following observations were made. Firstly, that the native GBM polysaccharide-TT conjugate did elicit a measurable, albeit weak, immunological response to the GBM polysaccharide as shown by an increase in binding of the GBM polysaccharide exhibited by the immume serum over the preimmune serum. Secondly, it is of interest to note that the N-Pr-GBM polysaccharide-TT conjugate was able to elicit antibodies cross-reactive with the native GBM polysaccharide, and that these cross-reactive antibodies were able to bind the heterologous GBM polysaccharide more effectively than antibodies raised to the homologous native GBM polysaccharide-TT conjugate. In all cases the binding of the GBM polysaccharide to the N-Pr-GBM polysaccharide-conjugate antisera was better than to its homologous conjugate antisera.

EXAMPLE 4

Further Immunization Tests in Mice

Immunization procedures

Female white CF1 mice (8–10 wk old) were immunized (3 times) intraperitoneally with polysaccharides and polysaccharide-TT conjugates in Freund's complete adjuvant (FCA) (Difco, Detroit, MI). The mice were divided into four groups of 10, 35, 35, and 10 and the groups were immunized (1°) respectively with 5 µg of the following antigens: N-Pr GBMP, N-Pr GBMP-TT conjugate N-Ac GBMP-TT conjugate and FCA. Five mice from each of the above groups (except the group immunized with N-Pr GBMP) were then bled 21 d following the injection, and the remainder were immunized again (2°) with 10 µg of the same antigens. After 11 d a number of mice (5, 15, 15 and 5) from the respective groups were exsanguinated and on the same day the remainder were immunized for a third time (3°) with 10 µg of the same antigens, except that 5 mice of the N-Ac GBMP-TT conjugate group were given the N-Pr GBMP-TT conjugate and 6 mice of the N-Pr GBMP-TT conjugate group were given the N-Ac GBMP-TT conjugate. The remaining mice were then exsanguinated 11 d after the 3° injection.

The following tests were conducted with the antisera.

Quantitative precipitin analyses

These experiments were carried out by the method of Kabat and Mayer. Aliquots (100 µL) of horse IgM were reacted in tubes with increasing concentrations of polysaccharides in a total volume of 200 µL (adjusted with PBS). The tubes were incubated at 4° C. for 2 d, centrifuged, and the quantity of antibody protein in the pellet was determined by the method of Lowry et al. (14).

The precipitin curves indicated that while a 20% loss of N-Ac groups diminished the antigenicity of the GBMP only marginally, more substantial losses had drastic effects on its antigenicity. Thus with between 67% and 87% loss of N-Ac the antigenicity of the GBMP disappeared completely. N-propionylation of the N-deacetylated GBMP was able to restore its antigenic properties. Although this effect was only small with half the sialic residues being N-proionylated, complete N-propionylation of the GBMP restored a substantial amount (40%) of its antigenicity.

Radioactive Antigen binding assay

This assay was carried out by a modification of the Farr technique using an extrinsically [$^3$H]-labeled GBMP antigen as previously described. The reaction mixture for the radioactive antigen-binding assay was obtained by mixing in Eppendorf polypropylene microtest tubes 25 μL of a solution containing 125 ng of [$^3$H]-labeled GBMP (100 cpm/ng), 25 μL of mouse antiserum and sufficient PBS to take the total volume to 550 μL. After incubation at 4° C. for 16 h, 500 μL of saturated (at 4° C.) ammonium sulfate (pH 7.0) was added to the tubes and they were agitated and left to stand at 4° C. for 30 min. The tubes were centrifuged at 15,000 rmp for 10 min and two aliquots of 400 μL were withdrawn from the tubes. The aliquots were mixed with 2 mL of water and a scintillant-containing xylene (ACS aqueous scintillant) and the mixtures were counted in a liquid scintillation counter.

ELISA

The wells of EIA microtitration plates were coated using a 10 µg/mL solution of high molecular weight GBMP in 0.05M sodium carbonate-bicarbonate buffer at pH 9.6 at 37° C. for 3 h and for a further 16 h at 4° C. After coating the plates were washed with 1% bovine serum albumin in PBS for 10 min at room temperature. The wells were then filled with 100 µL of serial 10-fold dilutions in PBS of mouse antisera and the plates left for 2 h at room temperature. The initial dilution of the antisera was 1:10. The IgG and IgM levels were determined using a Hybri-Clonal (TM) EIA Mouse Antibody Screening Kit (Kirkegaard and Perry Laboratories, Inc., Gaithersburg, MD) using peroxidase conjugated goat anti-mouse IgG and IgM antibodies and 2,2-azino-di-[3-ethyl-benzthiazoline sulfonate] in cacodylic buffer with hydrogen peroxide as the substrate. After 10 min the optical density at 414 nm was read.

IMMINIZATION RESULTS

It was readily observed that while antisera from the mice immunized repeatedly with the N-Pr GBMP and N-Ac GBMP showed no significant increase in binding to GBMP over that of the FCA control antiserum, the antisera induced in mice immunized with the N-Ac and N-Pr-GBMP-TT conjugates did exhibit substantial increases in binding of GBMP. Compared to the N-Pr GBMP-TT conjugate the N-Ac GBMP-TT conjugate induced in mice a more meagre but nevertheless measurable increase in the binding of GBMP with some evidence of a booster effect following the third injection. In contrast the N-Pr GBMP-TT conjugate produced a steadier and much more pronounced rise in GBMP binding with each successive injection, the booster effect being particularly noticeable following the third injection. Interestingly the N-Ac GBMP-TT conjugate was able to boost the response to GBMP in mice given two previous injections of the N-Pr GBMP-TT conjugate and this also proved to be true in the reverse case, where the mice were primed with the N-AC GBMP-TT conjugate and boosted with the N-Pr response to GBMP using the N-Pr GBMP-TT conjugate was a general phenomenon was evident from the evaluation of the individual mouse antisera induced by injection of this immunogen. A large booster effect was apparent in all the mice following both the second and third injections.

The relative amounts of IgG and IgM GBMP-specific antibodies involved in the total antibody response in the mice were determined by ELISA using a high molecular weight GBMP as the coating antigen, and following the addition of the mouse antisera, the IgG and IgM GBMP-specific antibodies were tagged using peroxidase conjugated goat anti-mouse IgG and IgM antibodies. ELISA end-point titrations were then conducted. Reciprocal end-point titers for IgG and IgM in a typical antiserum from a mouse injected three times with the N-Pr GBMP-TT conjugate were obtained and proved to be typical for all the mice injected in this way. The ratio of IgG to IgM in each antiserum was determined from their relative absorbances at 414 nm at a point in the curve equivalent to half the reciprocal end-point titers. An examination of the ELISA results indicated that the level of GBMP-specific IgG antibody was greatly increased with each successive injection of the N-Pr GBMP-TT conjugate, and that following the third injection, antibody of the IgG isotype predominated. This was a consistant phenomenon since similar and increasing levels of IgG were recorded for the individual mice injected with the N-Pr GBMP-TT conjugate. Of interest is the fact that this phenomenon was also demonstrated in mice in which the N-Pr GBMP-TT conjugate was used to boost the initial response to the N-Ac GBMP-TT conjugate and where the N-Ac GBMP-TT conjugate was used to boost mice primed with the N-Pr GBMP-TT conjugate. In contrast, although some GBMP-specific IgG antibody was detected in mice injected only with the N-Ac GBMP-TT conjugate it did not predominate and the total antibody level was much lower.

In the mice experiments the unconjugated N-Pr GBMP and N-Ac GBMP failed to give a measureable GBMP-immune response. However, similar to rabbits, the N-Pr GBMP-TT conjugate produced two populations of antibodies in mice, one specific for the N-Pr GBMP and the other cross-reactive with N-Ac GBMP. The binding of the GBMP to this latter population of antibodies induced by primary and booster immunizations of mice using the N-Pr GBMP-TT conjugate was ascertained and compared to the binding of the GBMP to antibodies induced in mice using the homologous N-Ac GBMP-TT conjugate. The results of these experiments clearly indicate that only the N-Pr GBMP-TT conjugate was able to induce in mice significantly enhanced levels of GBMP-specific antibodies. It was also possible to boost the level of these antibodies with successive immunizations which is indicative of a memory based on the participation on T-cells, and this fact is also substantiated by the large proportion of antibodies of the IgG isotype produced in this immune response. As this is the first report of an immunogen capable of consistently inducing GBMP-specific IgG antibodies, the N-Pr GBMP-TT conjugate must be considered an excellent candidate for a vaccine against meningitis caused by GBM organisms.

REFERENCES (1) Wyle, F. A., M. S. Artenstein, B. L. Brandt, D. L. Tramont, D. L. Kasper, P. Altieri, S. L. Berman, and J. P. Lowenthal. 1972. Immunologic response of man to group B meningococcal polysaccharide antigens. *J. Infect. Dis.* 126: 514.

(2) Jennings, H. J., and C. Lugowski. 1981. Immunochemistry of groups A, B and C meningococcal polysaccharide-tetanus toxoid conjugates. *J. Immunol.* 127: 1011.

(3) Jennings, H. J. 1983. Capsular polysaccharides as human vaccines. *Adv. Carbohydr. Chem. Biochem.* 41: 155.

(4) Mandrell, R. E., and W. D. Zollinger. 1982. Measurement of antibodies to meningococcal group B polysaccharide: low avidity-binding and equilibrium constants. *J. Immunol.* 129: 2172.

(5) Frosch, M., I. Gorgen, G. J. Boulnois, K. N. Timmis, and D. Bitter-Suermann. 1985. NZB mouse system for production of monoclonal antibodies to weak bacterial antigens: Isolation of an IgG antibody to the polysaccharide capsules of *Escherichia coli* KI and group B meningococci. *Proc. Nat. Acad. Sci.* 82: 1194.

(6) Finne, J., V. Finne, H. Deagostini-Bazin, and C. Goridis. 1983. Occurrence of α-2-8 linked polysialosyl units in a neural cell adhesion molecule. *Biochem. Biophys. Res. Comm.* 112: 482.

(7) Finne, J., M. Leinoren, and P. H. Makela. 1983. Antigenic similarly between brain components and bacteria causing meningitidis. *Lancet* ii: 355.

(8) Frasch, C. E. 1979. Non-capsular surface antigens of *Neisseria meningitidis. Semin. Infect. Dis.* 2: 304.

(9) Zollinger, W. D., R. E. Mandrell, J. M. Griffiss, P. Altieri, and S. Berman. 1979. complex of meningococcal group B polysaccharide and type 2 outer membrane protein immunogenic in man. *J. Clin. Invest.* 63: 836.

(10) Frasch, C. E., M. S. Peppler, T. R. Cate, and J. M. Zahradnik. 1982. Immunogenicity and clinical evaluation of group B *Neisseria meningitidis* outer membrane protein vaccines. *Semin. Infect. dis.* 4: 262.

(11) Jennings, H. J., C. Lugowski, and F. E. Ashton. 1984. Conjugation of meningococcal lipopolysaccharide R-type oligosaccharides to tetanus toxoid as a route to a potential vaccine against group B *Neisseria meningitidis. Infect. Immun.* 43: 407.

(12) Brandt, B. L., F. A. Wyle, and M. S. Artenstein. 1972. A radioactive antigen-binding assay for *Neisseria meningitidis polysaccharide antibody. J. Immunol.* 108: 913–920.

(13) Farr, R. S. 1958. A quantitative immunochemical measure of the primary interaction between I*BSA and antibody. J. Infect. Dis. 103: 239–262.

(14) Lowry, O. H., N. J. Rosebrough, A. L. Farr, and R. J. Randall. 1961. Protein measurement with the Folin phenol reagent. *J. Biol. Chem.* 193: 265.

We claim:

1. A modified B polysaccharide of *Neisseria meningitidis having sialic acid residue N-acetyl groups replaced with N-propionyl groups.*

2. An *E. coli* Kl capsular polysaccharide having the sialic acid residue N-acetyl groups replaced with N-propionyl groups.

3. The modified polysaccharide of claim 1 having a molecular weight within the range 10,000 to 50,000.

4. The modified polysaccharide of claim 1 having a degree of N-propionylation of from about 90 to 100%.

5. An antigenic conjugate comprising the modified group B polysaccharide of claim 1 conjugated to an immunologically-suitable protein carrier.

6. The antigenic conjugate of claim 5 wherein the polysaccharide and protein are covalently linked through a $$-CH_2-\overset{H}{N}-\text{protein}$$

linkage.

7. The antigenic conjugate of claim 5 wherein the protein is selected from tetanus toxoid or diphtheria toxoid.

8. A cross-reactive vaccine comprising the conjugate of claim 5 and an injectable carrier.

* * * * *